(12) United States Patent
Genovese (10) Patent No.: US 7,749,440 B1
(45) Date of Patent: Jul. 6, 2010

(54) APPARATUS FOR CHEMICAL DETECTION TRAINING

(75) Inventor: James A. Genovese, Street, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1101 days.

(21) Appl. No.: 11/340,814

(22) Filed: Jan. 12, 2006

(51) Int. Cl.
*G01N 33/00* (2006.01)

(52) U.S. Cl. .................. 422/61; 436/104; 436/165; 436/169; 73/863.12

(58) Field of Classification Search .............. 422/56, 422/58, 61; 436/104, 164, 169; 73/863.12
See application file for complete search history.

(56) References Cited

U.S. PATENT DOCUMENTS 5,035,860 A * 7/1991 Kleingeld et al. ............ 422/61
5,726,068 A * 3/1998 Rivin et al. ................. 436/167
5,814,524 A * 9/1998 Walt et al. .................. 436/518
6,770,485 B2 * 8/2004 Knezevic et al. ............. 436/86

OTHER PUBLICATIONS

Peter Spaeth, "Catalog of Chemicals Contained in Chemical Detector, Decontaminating, and Training Kits", Jul. 1992, U.S. Army Armaments Munitions Chemical Command, pp. 9-19.*
Internet, "www.danoland.com" and "en.wikipedia.org", no date.*

* cited by examiner

*Primary Examiner*—Lyle A Alexander
(74) *Attorney, Agent, or Firm*—Ulysses John Biffoni (57) ABSTRACT

Methods and apparatus for chemical warfare agent detection training are provided. More particularly, methods and apparatus are provided to simulate the detection of low volatility chemical warfare agents by simulating the use of currently fielded U.S. Army detection kits without exposure to hazardous agents. A simulant is disposed in a sample heating assembly. The sample heating assembly is placed over a detection window of a detector, and the simulant is heated in order to make a simulated detection.

8 Claims, 5 Drawing Sheets

APPARATUS FOR CHEMICAL DETECTION TRAINING

GOVERNMENT INTEREST

The invention described herein may be manufactured, licensed, and used by or for the U.S. Government.

CROSS RELATED APPLICATION

This application is related to commonly assigned, application Ser. No. 10/633,773, filed Aug. 4, 2003, titled "SAMPLE HEATER ASSEMBLY AND METHOD OF USE THEREOF," now issued U.S. Pat. No. 7,036,388 the entire contents of which are incorporated herein by reference.

TECHNICAL FIELD OF THE INVENTION

The present invention relates generally to chemical detection and in particular the present invention relates to chemical detection training.

BACKGROUND OF THE INVENTION

Low volatility agents (LVA), particularly in the chemical warfare agent nerve agent class of VX, pose a very toxic and persistent hazard to conventional military forces and possibly to civilian populations. These chemical warfare agents are potentially employed as a tactical or terror weapon in various military scenarios, such as being deployed in military actions for effective terrain denial, using a variety of dissemination mechanisms including grenades, mortars, mines, rockets, bombs, long-range projectiles, and missiles. Although these low volatility agent hazards normally produce minimal vapor inhalation hazard, if properly configured, high explosive mechanisms and special configuration sprayers can produce airborne droplets and aerosols in addition to significant liquid ground deposition contamination. In such forms, these hazards are generally liquids and exhibit physical/chemical properties quite different from respiratory hazard chemical warfare agents.

Low vapor pressure hazards, such as low volatility agents, can be detected with a low volatility hazard detector (LVHD), such as described in U.S. Pat. No. 7,036,388, which includes a sample heater assembly that can be used with an M256 Chemical Agent Detector to effectively vaporize one or more low volatility agents for detection thereof. However, low volatility hazard detectors can be difficult to use without proper training.

For the reasons stated above, and for other reasons stated below which will become apparent to those skilled in the art upon reading and understanding the present specification, there is a need in the art for apparatus and methods that facilitate training in the use of low volatility hazard detectors.

SUMMARY

The above-mentioned problems with low volatility hazard detectors and other problems are addressed by the present invention and will be understood by reading and studying the following specification.

For one embodiment, the invention provides a training method including disposing a simulant in a sample heating assembly, positioning the sample heating assembly over a detection window of a chemical detector, and heating the simulant for simulating the heating and resulting vaporization of a sample of an actual agent.

Further embodiments of the invention include methods and apparatus of varying scope.

DETAILED DESCRIPTION

In the following detailed description of the invention, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and chemical changes may be made without departing from the scope of the present invention. The following detailed description is, therefore, not to be taken in a limiting sense, and the scope of the present invention is defined only by the appended claims and equivalents thereof.

Figure 1:
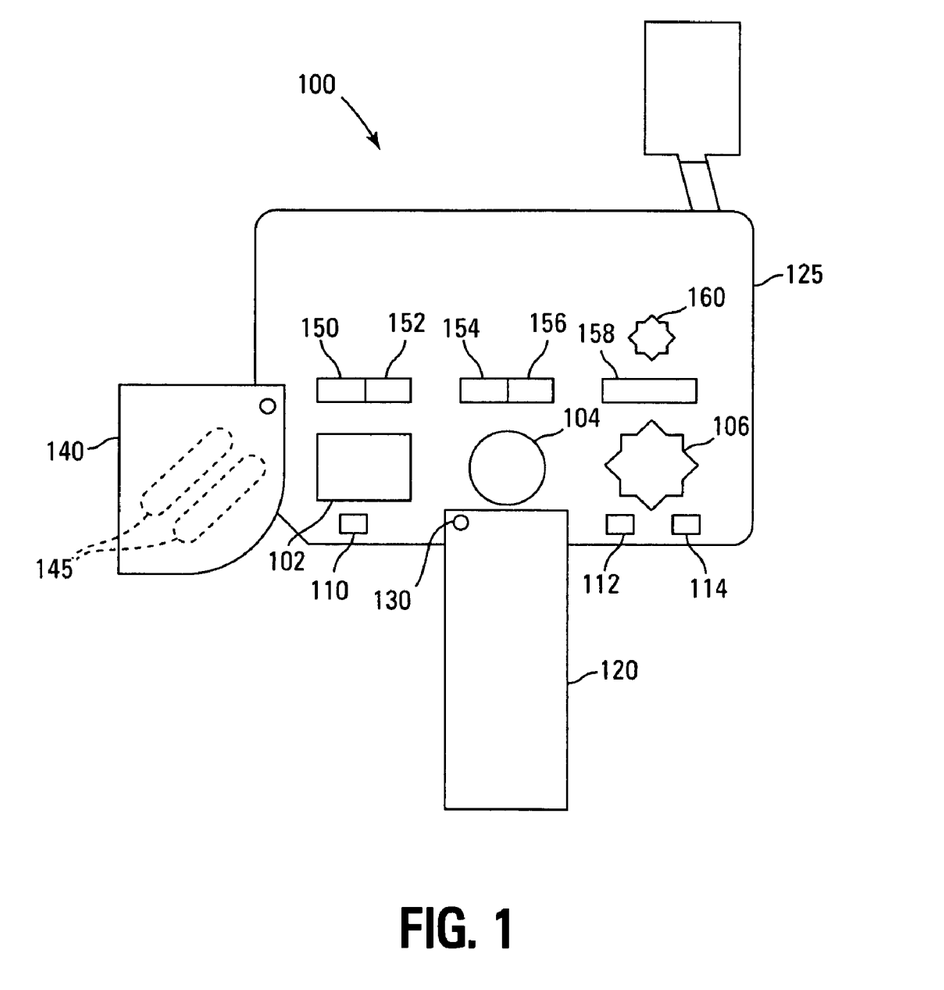
FIG. 1 is a back view of an embodiment of a chemical detector, where color comparison is performed, according to an embodiment of the invention.

FIG. 1 is a back view of a detector 100, according to an embodiment. For one embodiment, detector 100 is configured for training and may be an M256 TRAINS (Training/Simulator) chemical detection simulator ticket and is a portion of a chemical detection training kit. The M256 TRAINS chemical detection simulator is described in CRDEC Technical Report, CRDEC-SP-049, "Catalog of Chemicals Contained in Chemical Detector, Decontaminating, and Training Kits," Peter Spaeth, Compliance Directorate, July 1992. Other components of the chemical detection training kit are described below. Differences between the M256 TRAINS chemical detection simulator and the M256 Chemical Agent Detector are also described below.

Detector 100 includes detection windows 102, 104, and 106. The backsides of which are shown in FIG. 1. For one embodiment, detection window 102 may be used to simulate the detection of blister agents, such as a liquid mustard agent (e.g., HD mustard), detection window 104 to simulate the detection of blood gas, and detection window 106 to simulate the detection of nerve agents (e.g., VX or GB Sarin). For another embodiment, detection windows 102, 104, and 106 are respectively square shaped, circular shaped, and star shaped. For some embodiments, a M8 detection comparator 110, such as red, is located adjacent to the detection window 102 and M8 detection comparator 112 and 114, e.g., respectively green and yellow or gold, are located adjacent detection window 106. The use of these color comparators is discussed below. Because detector 100 is configured as a chemical detection simulator, detection windows 102, 104, and 106 are respectively for simulating the detection of different types of chemical agents, e.g., simulating detection of blister agents using window 102, blood gas using window 104, and nerve agents using window 106. However, as a simulator there is no actual exposure to any potentially hazardous environmental sample such as one containing chemical warfare agents. In addition, actual exposure of the detector ticket to the simulants is not required because the detector tickets are predesigned to provide a specific type of response. For training purposes, the simulants are only used to provide an initial response from the M8 or M9 paper, which is then either confirmed as "positive" or rejected as "false positive" by the type of detector ticket used, for example, M256 TRAINS T-400. T-401 or T-402.

For other embodiments, a protective strip 120 may be pivotally attached to a substrate 125 of detector 100, where protective strip 120 pivots about a pivot 130 for covering one or more of detection windows 102, 104, and 106 at a time. For one embodiment, a heating element 140 is removably attached to substrate 125. Heating element 140 may include any appropriate heating mechanism for effectively simulating vaporizing the low volatility agent for detection. For one embodiment, heating element 140 includes a Mustard Agent Heater Assembly of the M256 Chemical Agent Detector Kit, as described in U.S. Pat. No. 7,036,388. For training purposes, heating element 140 is used for simulating heating of a low volatility agent, but no vapor detection is performed for the simulation. The heater ampoules are functioned just to simulate the process but serve no other purpose but to mimic the heating process when using a real M256 detector. The simulants are discussed in greater detail below.

Heating element 140 may include two reactant vials 145, e.g., containing cupric chloride (0.4 grams/vial) and a pad, e.g., containing aluminum powder (0.285 grams/pad). When the cupric chloride vials are broken an exothermic chemical reaction results, producing heat. The reactant vials 145 may be encased in a plastic cover on a front side of detector 100 to contain the reaction components and an aluminum foil backing to assist in effective heat transfer of the chemical reaction to a sample.

Figure 2:
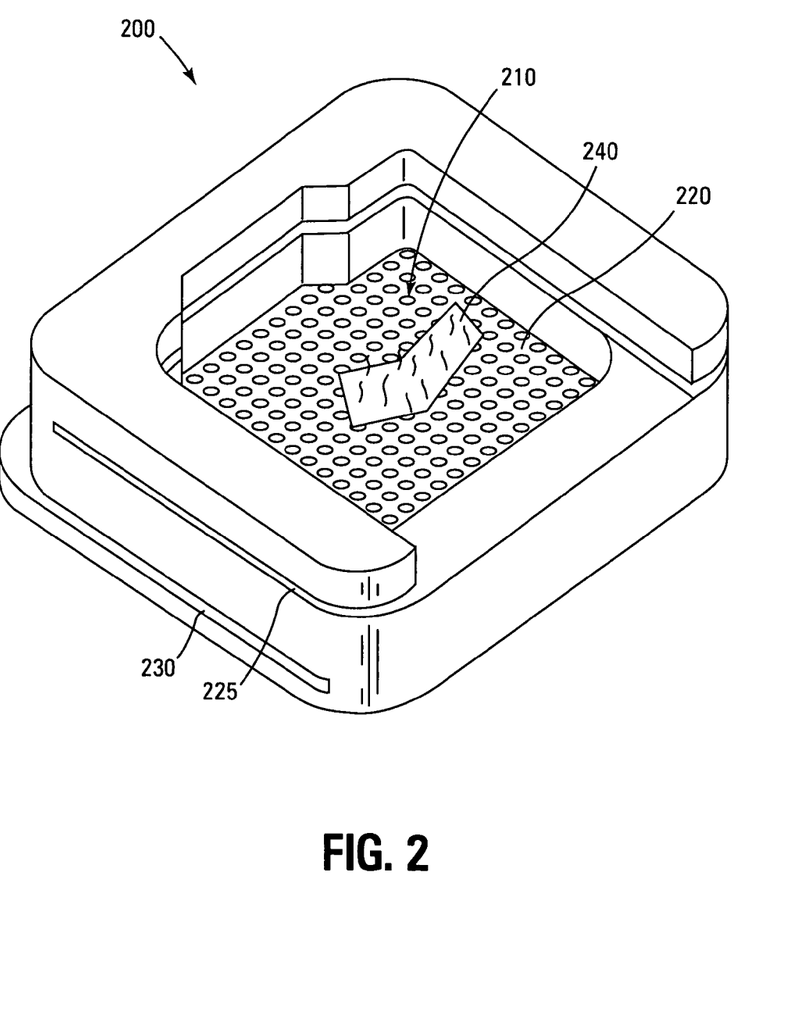
FIG. 2 illustrates an embodiment of a sample heater assembly, according to another embodiment of the invention.
Figure 3:
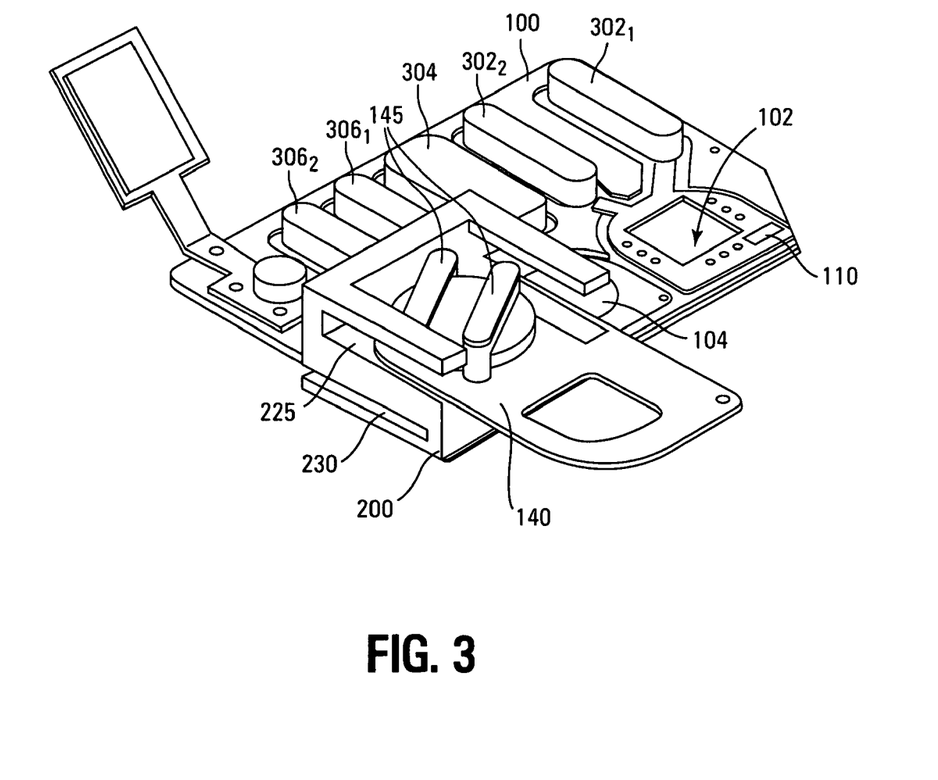
FIG. 3 is a front view of the chemical detector of FIG. 1, with sample heater assembly of FIG. 2 attached according to another embodiment of the invention.

FIG. 2 illustrates a sample heater assembly 200 that is fully described in U.S. Pat. No. 7,036,388. For one embodiment, sample heater assembly 200 is a portion of the chemical detection training kit along with detector 100. For actual M256A1/A2 chemical detection kits sample heater assembly 200 is used in combination with detector 100 as shown in FIG. 3, a front view of detector 100, to increase the effective vapor pressure of low volatility hazardous liquids, particularly chemical warfare agents, such as VX. For the present invention it is only used for simulation purposes.

For training, heater assembly 200 is used in combination with detector 100, configured for training, to simulate heating of the low volatility hazardous liquids. When configured for training, detection windows 102, 104, and 106 contain M256 color indicators that are observable from the front of detector 100. Ampoules 302, 304, and 306 (FIG. 3) are respectively fluidly coupled to windows 102, 104, and 106 and contain reagent liquids (or colorimetrics) that when released into the respective windows, by crushing the respective ampoules, cause the detection windows to change color to simulate the presence or absence of a hazardous liquid. For one embodiment, the M256 color indicators are selected or pre-engineered to cause the detection windows to change color to simulate the presence or absence of a hazardous material. The M256 color indicators in the windows and the reagents are discussed in more detail below. For one embodiment, detector 100, configured for training, combined with sample heater assembly 200 is a Low Volatility Hazard Detector M256 TRAINS (LVHD M256 TRAINS).

Sample heater assembly 200 has a sample containment reservoir 210. For one embodiment, sample heater assembly 200 includes a screened section 220 of the sample containment reservoir 210. For another embodiment, sample heater assembly 200 includes slots 225 and 230.

As shown in FIG. 3, a portion of detector 100 is received in slot 230 so that sample heater assembly 200 is positioned over one of the detection windows 102, 104, or 106, such as detection window 106, as in FIG. 3. Then, for example, a chemical detection paper 240, containing a sample, e.g., a liquid, such as a simulant of an actual hazardous liquid, absorbed by the paper or a solid attached to the paper, is disposed in sample containment reservoir 210, as shown in FIG. 2. Heating element 140 is removed from detector 100 and is inserted into slot 225 so as to cover sample containment reservoir 210, as shown in FIG. 3. For one embodiment, chemical detection paper 240, containing a sample, is inserted in slot 225 of sample heater assembly 200 so as to span sample containment reservoir 210 and heating element is also inserted into slot 225. This enables heating element 140 to be closer to chemical detection paper 240, thereby improving heat transfer to chemical detection paper 240. With heating element 140 covering sample containment reservoir 210, the vials 145 face a user of sample heater assembly 200, and the aluminum foil backing of the vials 145 faces into sample containment reservoir 210 and contacts the portions of sample heater assembly 200 surrounding sample containment reservoir 210. Samples can go into reservoir or like M8 and M9 be slid directly under the heater (as shown in FIG. 5(*d*) of LVHD TRAINS Tech Report, page 6) very close to foil heater surface to maximize heating.

In order to simulate the detection process, the to user crushes vials 145, to simulate causing an exothermic chemical reaction that heats the sample in a real chemical detector contained by chemical detection paper 240. The user also releases a liquid reagent by crushing ampoules 302, 304, or 306 (FIG. 3) that are respectively fluidly coupled to windows 102, 104, and 106. The reagent produces a predetermined color change in its corresponding window depending on the type of training detector ticket used (for example M256 TRAINS T-400, T-401, T-402 tickets). Note that the reagent is released from ampoules 306 and flows into window 106 in the example of FIG. 3.

The training liquid reagents do not react with any vapors that may be given off while heating simulants for simulating heating of a low volatility agent, but are selected to produce the same colors that occur in the presence or absence of an actual hazardous liquid. No exposure of actual chemical agents is necessary to carry out an M256 Trains simulation. In addition, the simulants are only exposed to the M8 or M9 paper, they do not actually have to be exposed to the M256 TRAINS detector tickets.

For another embodiment, M256 color comparators 150, e.g., purple-blue, and 152, e.g., red-purple, are located above window 102, as shown in FIG. 1, and correspond to the color changes in the presence of blister agents, e.g., respectively of mustard (H or HD) and phosgene oxime (CX). No color change in window 102 in response to the reagent indicates that there is no blister agent present, e.g., no hazard. For one embodiment, M256 color comparators 154, e.g., pink, and 156, e.g., blue, are located above detection window 104 (FIG. 1) and correspond to the color changes in the presence of blood agent. No color change or a color change to tan indicates no hazard. For other embodiments, M256 color comparator 158, e.g., clear, located above window 106 (FIG. 1)

corresponds to the presence a nerve agent. Color comparator 160, e.g., blue-green, indicates no hazard.

Configuring detector 100 for training involves disposing reagent liquids in ampoules 302, 304, and 306 and disposing indicator reagent in detection windows 102, 104, and 106. The following non-limiting examples illustrate using a detector 100, configured for training, for simulating detection of the presence (POSITIVE) or absence (NEGATIVE) of an actual hazard:

Different detectors 100, configured for training, are respectively used to simulate the detection of the presence and absence of an actual blister agent. For a detector 100, configured for training and to simulate the detection of the presence of an actual blister agent, such as an M256 TRAINS T-402, a liquid reagent released from ampoules 302 into window 102 will change to the color produced in the presence of blister agents, such as a liquid mustard agent (e.g., HD mustard), upon contacting the indicator in window 102, and will match either color comparator 150 or 152 to indicate a POSITIVE. For a detector 100, configured for training, and to simulate the absence of an actual blister agent, such as an M256 TRAINS T-400, a liquid reagent released from ampoules 302 into window 102 will not match either color comparator 150 or 152 to indicate a NEGATIVE, e.g., a NEGATIVE may be indicated by no color change. For one embodiment, e.g., for an M256 TRAINS T-400, the liquid reagent in both ampoules 302 may be water and methanol and the corresponding indicator in window 102 silica gel paper. For another embodiment, e.g., for an M256 TRAINS T-402, the liquid reagent in ampoule $302_1$ may be water and potassium carbonate, the liquid reagent in ampoule $302_2$ thymolphthalein and methanol, and the corresponding indicator in window 102 silica gel paper. For another embodiment, the liquid reagent may be released sequentially from ampoules $302_1$ and $302_2$, e.g., ampoule $302_2$ followed by ampoule $302_1$.

To simulate the detection of the presence or absence of blood agent, a colorimetric released from ampoule 304 into window 104 will change to the color produced in the presence of blood upon contacting the indicator in window 104 and will match either color comparator 154 or 156 to indicate a POSITIVE or will not match either color comparator 154 or 156 to indicate a NEGATIVE, e.g., a NEGATIVE may be indicated by no color change. For one embodiment, the liquid reagent in ampoule 304 may be water and methanol and the corresponding indicator in window 104 silica gel paper. For another embodiment, the liquid reagent in ampoule 304 may be water and potassium carbonate and the corresponding indicator in window 104 thymolphthalein and methanol.

Different detectors 100, configured for training, are respectively used to simulate the detection of the presence and absence of nerve agents (e.g., VX or GB Sarin). For a detector 100, configured for training and to simulate the detection of the presence of nerve agents (e.g., VX or GB Sarin), such as an M256 TRAINS T-401, a liquid reagent released from ampoules 306 into window 106 will change to the color produced in the presence of actual nerve agents (e.g., VX or GB Sarin) upon contacting the indicator in window 106 and will match color code 158, which is white or colorless, to indicate a POSITIVE. For a detector 100, configured for training and to simulate the absence of a nerve agent, such as an M256 TRAINS T-400, a reagent liquid released from ampoules 306 into window 106 will match M256 color comparator 160 to indicate a NEGATIVE, which is a blue color. For one embodiment, e.g., for an M256 TRAINS T-401, the liquid reagent in ampoule $306_1$ may be tris-(hydroxymethyl)-aminomethane, hydrochloric acid, and aerosol-OT (AOT, sodium bis(2-ethyl-1-hexyl)sulfosuccinate), the liquid reagent in ampoule $306_2$ 2,6-dichloroindophenyl acetate and ligorine, and the corresponding indicator in window 106 an unimpregnated glass filter disc. For another embodiment, e.g., for an M256 TRAINS T-400, the reagent liquid in ampoule $306_1$ may be tris-(hydroxymethyl)-aminomethane, hydrochloric acid, and aerosol OT, the reagent liquid in ampoule $306_2$ 2,6-dichloroindophenyl acetate and ligorine, and the corresponding indicator in window 106 horse serum cholinesterase and gelatin impregnated in filter paper. For another embodiment, the reagent liquid may be released sequentially from ampoules $306_1$ and $306_2$, e.g., ampoule $306_1$ followed by ampoule $306_2$.

Note that for one embodiment, M8 color comparator 110 shown in FIG. 1 may also be disposed on the front of detector 100 adjacent window 102 as shown in FIG. 3. Similarly, M8 color comparators 112 and 114 may also be disposed on the front of detector 100 adjacent window 106. Note that the M8 color comparators 112 and 114 disposed on the front of detector 100 are covered by sample heater assembly 200 in FIG. 3.

Figures 4A, 4B:
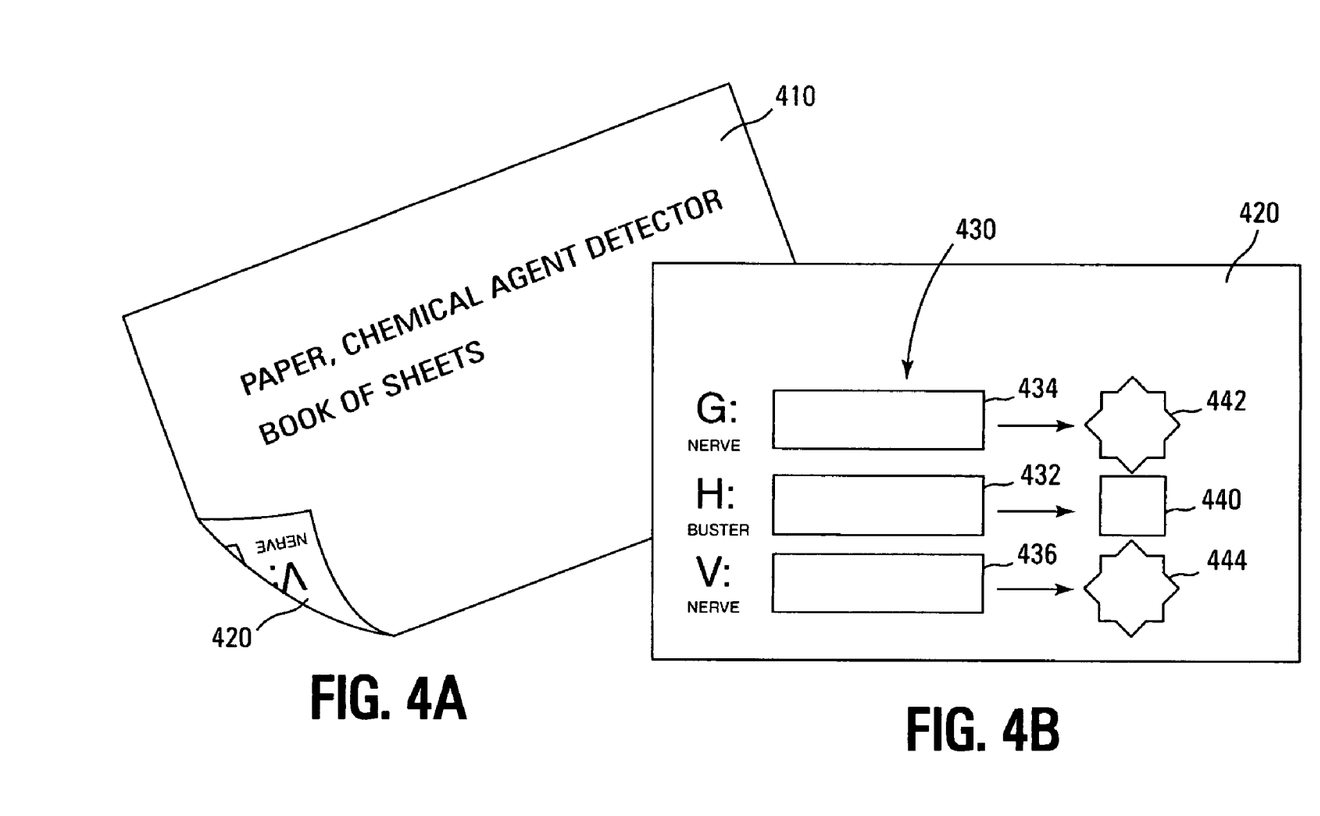
FIGS. 4A and 4B respectively illustrate a front side and a backside of an embodiment of a cover of a booklet of liquid chemical detection paper, according to another embodiment of the invention.

For one embodiment, chemical detection paper 240 is a portion of the chemical detection kit or the chemical detection training kit of which detector 100 and sample heater assembly 200 are portions. For another embodiment, chemical detection paper 240 may be M8 Detection Papers (Paper, Chemical Agent Detector, VGH, ABC-M8), described in army supply Bulletin SB 3-6665-2. M8 Detection Paper is typically included as pages of a booklet. FIGS. 4A and 4B respectively illustrate a front side 410 and a backside 420 of a cover of such a booklet, according to another embodiment.

Prior to disposing chemical detection paper 240 in sample containment reservoir 210, as shown in FIG. 2, the user dips at least a portion of the M8 Paper into a suspect liquid, thereby absorbing the liquid, any particular color change is matched to the color presented with the M8 detection color comparators (FIG. 4B) key 430 disposed on backside 420 of the cover. Any color match indicates the possible presence of an agent hazard or of a simulant for simulating that agent hazard. After a color change from the M8 Paper, the user inserts the M8 Paper 240 into the sample heater assembly 200, as described above.

For one embodiment, colors 432 (e.g., red), 434 (e.g., yellow or gold), and 436 (e.g., green) of color key 430 respectively match M8 detection color comparators 110, 112, and 114 on the back of detector 100 (FIG. 1) or front of detector 100 (FIG. 3). This acts to assist the user to select, or confirm, the appropriate detection window from detection windows 102 and 106 of detector 100. It should be noted that current fielded M256 Detectors (detector 100) do not have the M8 color comparators on the front and back of the M256 detector. This disclosure is an improvement over what now exists. The sample heater assembly 200 would then be placed over that detection window (FIG. 3). For another embodiment, graphical symbols M256 detection window shape icons 440, 442, and 444 are formed on backside 420 of the cover and respectively correspond to colors 432, 434, and 436, which are the M8 color comparators 430. Graphical symbol 440 (square) has substantially the same shape as detection window 102 (FIG. 1) and graphical symbols 442 and 444 (star), for one embodiment, each have substantially the same shape as detection window 106 (FIG. 1). This further assists the user to select, or confirm, the appropriate detection window from detection windows 102 and 106 of detector 100. Note that M8 detection color comparator 432 (e.g., red) relates to square blister icon 440 to the right of color key 430 and indicates the shape of window 102 and where to place sample heater assembly 200. M8 detection color comparator 434 (e.g., yellow or gold) relates to the starred nerve icon 442 to the right of M8 color key 430. M8 detection color comparator 436 (e.g., green) also relates to a starred nerve agent icon 444 to the right of M8 color key 430. It should be noted that the current fielded M8 does not have shape icons next to the M8 color comparators as provided in the present invention. The cross comparison of the new M8 paper with M256 detector shape icons added and the new M256 LVHD TRAINS with M8 color comparators added is unique and allows for simple processing of both detection components when integrated in the M256 LVHD TRAINS system.

For another embodiment, the graphical symbols 440, 442, and 444 (M256 detection window shape icons) aid in the selection of the proper detection window as follows: The color of the M8 Paper that results from absorbing a liquid sample, such as chemical warfare agent or its simulant, is matched to a color of M8 detection color comparator key 430, and the shape of the detection window is determined from the graphical shape corresponding to the matched color. Alternatively, M8 color comparators 110, 112, and 114 of detector 100 aid in the selection of the proper detection window as follows: The color of the M8 Paper that results from absorbing a liquid sample is matched to an M8 color comparator adjacent one of the detection windows of detector 100.

Figure 5A:
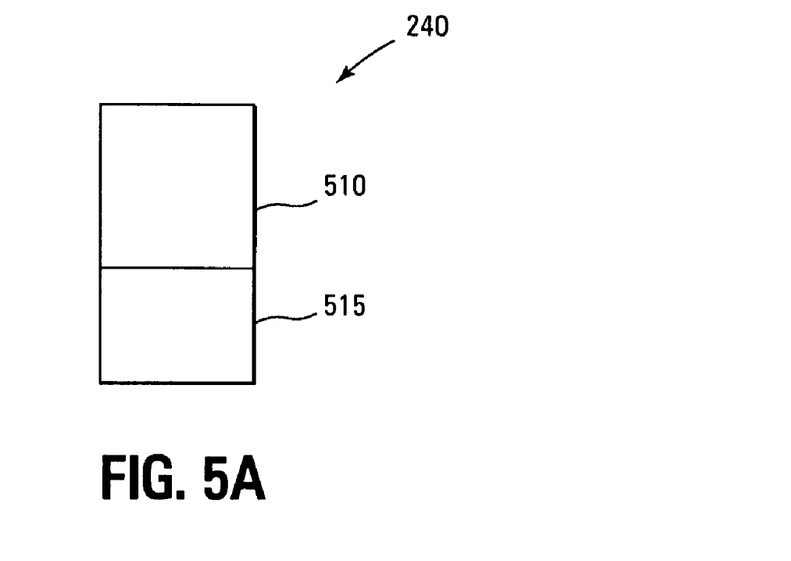
FIGS. 5A and 5B respectively illustrate a front side and a backside of an embodiment of chemical detection paper, according to another embodiment of the invention.
Figure 5B:
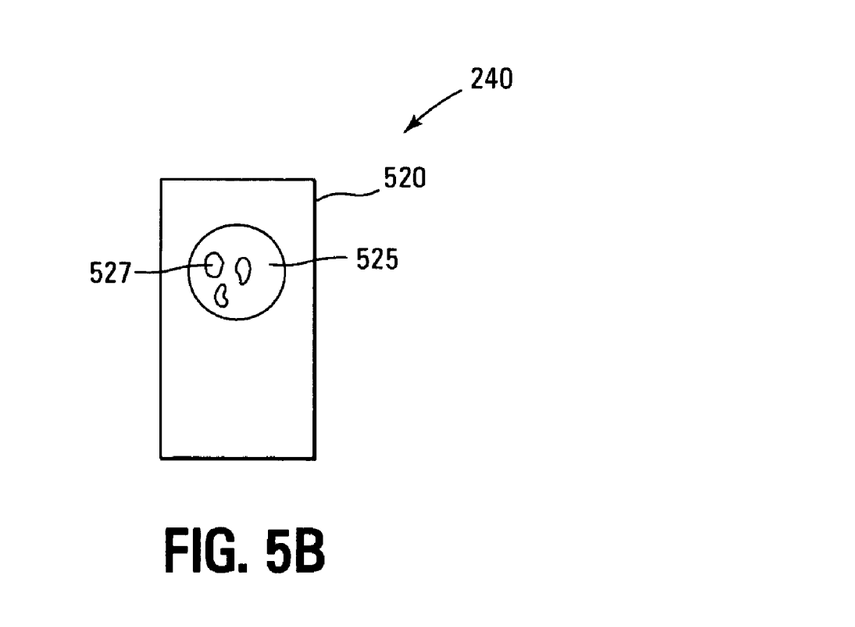

FIGS. 5A and 5B respectively illustrate a front side 510 and a backside 520 of chemical detection paper 240, such as M9 Chemical Detection Paper, according to another embodiment. Front side 510 includes a single die, e.g., SR 119, that changes color, e.g., to red, when it absorbs liquid chemical agent, such as nerve agent or blister agent. A portion 515 of front side 510 has been exposed to liquid chemical agent and has changed its color in response to the liquid chemical agent. Backside 520 includes a sticky portion 525 that is covered when not in use. Sticky portion 525 facilitates sampling of solid chemical agents. In operation, the sticky portion is exposed and adheres to solid sample particles 527.

In order to train the user in the operation of the chemical detection kit without exposing the user to hazardous chemical agents, the chemical detection training kit includes simulants, chemical detection paper 240, such as M8 Detection Papers in a booklet, as described above, and/or M9 Detection papers, as described above, sample heater assembly 200, and detector 100 configured for training. Note that when configured for training, ampoules 302, 304, and 306 contain liquid reagents that when released into contact with an indicator in the detection window, turns a color without a vapor being present to simulate a POSITIVE or that either changes color or does not change color to simulate a NEGATIVE.

For one embodiment, the simulants are compounds that cause chemical detection paper 240 to indicate a false positive in the presence of an interferent liquid, but appears as a detection indicating a POSITIVE for simulation purposes. For example, a simulant, such as benzene or xylene (GOOF OFF) available from The Valspar Corporation, Minneapolis, Minn., USA), causes M8 Detection Paper to turn color 432, e.g., red, of FIG. 4B, and M9 (FIG. 5A) paper to change its color, e.g., to red, and thus simulates a blister agent, such as mustard HD. Another simulant, such as glycol (e.g., brake fluid) or N—N diethyl m toluamide (DEET) (Deep Woods OFF manufactured by SC Johnson, Inc., Racine, Wis. USA), causes M8 Detection Paper to turn color 436, e.g., green, of FIG. 4B, and M9 paper (FIG. 5A) to change its color, e.g., to red, and thus simulates a nerve agent, such as VX. Another simulant, such as ammonia-containing window spray, causes M8 Detection Paper to turn color 434, e.g., yellow or gold, of FIG. 4B, and M9 paper (FIG. 5A) to show no reaction, and thus simulates a nerve agent, such as GB Sarin. Note that M9 paper changes to red in response to actual GB Sarin. For another embodiment, fumed silica or the like, can be used to simulate a hazardous solid. For one embodiment, liquid simulants are contained in color-coded jars, e.g., white, green, and blue jars, to assist trainer in organizing training scenarios.

In actual use, chemical detection paper 240 including its sample is placed in sample heater assembly 200, as shown in FIG. 2, or direct emplacement in slot 225 or as shown in FIG. 5(d) pg 6 of LVHD TRAINS report, which is positioned above the appropriate detection window of detector 100, configured as an actual chemical detector, as shown in FIG. 3. Chemical detection paper 240, including its sample, is heated so as to vaporize the sample, and a liquid reagent is released from the ampoule corresponding to the detection window to ascertain whether the sample is a hazardous chemical agent, as described above.

For one embodiment, the training kit includes a plurality of detectors 100, each configured for training, such as a plurality of M256 TRAINS, e.g., by containing a liquid reagent in one or more of its ampoules 302, 304, and 306, and a corresponding detection indicator in one or more of its detection windows 102, 104, and 106. For another embodiment, plurality of M256 TRAINS include M256 TRAINS T-400, T-401, T-402, etc. Each training detector 100 so configured is packaged with a sample heater assembly 200 and a liquid specific for detection papers simulant to form an integrated training packet of the training kit. The liquid reagent of that detector 100 may change color to simulate a POSITIVE or a NEGATIVE for that simulant when in contact with the corresponding indicator. Note that for one embodiment, an M256 TRAINS and a sample heater assembly 200 form an LVHD M256 TRAINS. Therefore, for this embodiment, the training kit includes a plurality of LVHD M256 TRAINS, each packaged with a specific simulant designating a simulated agent hazard.

Simulating a POSITIVE means to simulate the presence of a hazardous liquid simulated by a particular simulant. For example, if the simulant is xylene for simulating a blister agent, such as mustard HD, the liquid reagent and indicator on the detection window will be such as to turn the same color as the color in window 102 (FIG. 1) in the presence of an actual blister agent and will either match color comparator 150, e.g., purple-blue, or color code 152, e.g., red-purple, located above window 102, as shown in FIG. 1. If the simulant is DEET for simulating a nerve agent, such as VX, the liquid reagent and indicator will be such as to turn the same color as the color in window 106 (FIG. 1) in the presence of actual VX and will match M256 color comparator 158, e.g., clear, located above window 106, as shown in FIG. 1. If the simulant is window cleaner for simulating a nerve agent, such as GB Sarin, the liquid reagent and indicator will be such as to turn the same color as the color in window 106 (FIG. 1) in the presence of actual GB Sarin and will match M256 color comparator 158, e.g., clear, located above window 106, as shown in FIG. 1.

Simulating a NEGATIVE means to simulate the absence of the hazardous liquid simulated by that simulant. For example, for xylene for simulating a blister agent, the liquid reagent and indicator emplaced on the detector window will be such as to turn the same color as the color in indicator window 102 (FIG. 1) in the absence of an actual blister agent, e.g., clear. If the simulant is DEET for simulating a nerve agent, such as VX, the liquid reagent and indicator will be such as to turn the same color as the color in window 106 (FIG. 1) in the absence of VX, e.g., blue-green, and will further match M256 color comparator 160 (FIG. 1). If the simulant is window cleaner for simulating a nerve agent, such as GB Sarin, the liquid reagent and indicator will be such as to turn the same color as the color in window 106 (FIG. 1) in the absence of GB Sarin, e.g., blue-green, and will further match M256 color comparator 160 (FIG. 1). For other embodiments, water may be used as a simulant for simulating a NEGATIVE for either a blister agent or a nerve agent.

For training, a training packet containing an LVHD M256 TRAINS having a liquid reagent and indicator for simulating one of the training scenarios described above and a simulant is selected. The user dispenses the simulant on a surface and contacts the simulant with chemical detection paper 240. If chemical detection paper 240 is M8 Detection Paper and if the simulant is simulating the possibility of a hazardous liquid, the detection paper turns one of colors indicated on the M8 color comparator 432, 434, or 466 of FIG. 4B. Note that the simulant, e.g., water, may be selected so that the chemical detection paper 240 does not turn one of M8 colors 432, 434, or 466 of FIG. 4B in order to simulate a situation where there is not a possibility that a hazard is present, therefore producing a NEGATIVE.

Note that for actual chemical detection, the color change of detection paper 240, M8 or M9, only indicates the possibility of a hazardous liquid because some liquids, as mentioned above, cause detection paper 240 to change color, thereby causing a false positive. Therefore, a detector 100, configured for actual use, and a sample heater assembly 200, e.g., an LVHD M256, is used to determine whether there is a hazard.

To simulate the use of an LVHD M256, the appropriate detection window of the M256 TRAINS portion of the LVHD M256 TRAINS is determined, as described above, by comparing the color of the M8 paper to the M8 detection color comparators 110, 112, or 114 on detector 100 (FIG. 1) or matching the color of the paper to one of the colors 432, 434, or 466 of M8 detection color comparator 430 of FIG. 4B and determining the shape of the detection window from the graphical shape corresponding to the matched color or both. The M8 paper, including its simulant, is placed in sample containment reservoir 210 of sample heater assembly 200, as shown in FIG. 2, or into slot 225 of sample heater assembly 200, which is positioned above the appropriate detection window of detector 100, configured for training, as shown in FIG. 3. Heating element 140 is removed from detector 100 and is inserted over sample containment reservoir 210, as shown in FIG. 3. Note that in one embodiment, the M8 paper and heating element 140 are both inserted into slot 225 of sample heater assembly 200. Vials 145 are broken, causing an exothermic chemical reaction that heats the simulant, thereby simulating the heating of an actual sample. However, the training version of detector 100, e.g., an M256 TRAINS, does not analyze any vapors that may result from heating the simulant.

The M256 TRAINS includes a liquid reagent and indicator that do not react with any vapors that may result from heating the simulant. Releasing a liquid reagent into contact with an indicator and observing any color change, simulates whether the simulant simulates a hazard. Note that there is no reaction between the simulant and the liquid reagent and/or indicator in the detector. Moreover, the simulants are not explosive under the training conditions and have little or no adverse effect on the environment. Vapors generated from heating the simulants are not toxic to the user.

For another embodiment, M9 Detection Paper may be used. For example, if a solid simulant, such as fumed silica, is used, the sticky portion 525 (FIG. 5B) is brought in contact with the solid simulant. The paper, including the solid simulant, is disposed in sample heater assembly 200, which is positioned above one of the detection windows of a detector 100, configured for training, as shown in FIG. 3. The solid simulant is then heated, as described above. Releasing the liquid reagent into contact with the corresponding indicator simulates determining whether a hazard is present, but there is no interaction between any vapors from the heated sample and the liquid reagent and/or indicator.

M9 Detection Paper may also be used for liquid simulants to simulate the possibility of a hazard. For example, the M9 paper is brought in contact with the liquid simulant. If the paper changes color, there is possibility of a hazard, but there is no indication of the type of hazard, e.g., whether the hazard is a nerve agent or blister agent. The M9 paper, including the simulant, is disposed in sample heater assembly 200, which is positioned above one of the detection windows of a detector 100, configured for training, as shown in FIG. 3. The simulant is then heated, as described above. Releasing the liquid reagent into contact with the indicator simulates determining whether a hazard is present, but there is no interaction between any vapors from the heated sample and the liquid reagent and/or the indicator. Note that M9 paper does provide an indication as to which detection window should be used. Note that if the simulant is window cleaner, the M9 paper will not show a reaction (change its color).

For various embodiments, the training scenarios are denoted by codes. For example, a code T-800 simulates a NEGATIVE for a nerve or blister agent. For a code T-800 the simulant is water; M8 and M9 chemical detection paper is used; and the detector an M256 TRAINS T-400. Note that neither M8 nor M9 paper reacts with water, thus the M8 or M9 paper is sufficient for indicating the NEGATIVE, so there is no need to use the M256 TRAINS T-400. However, the M256 TRAINS T-400 is still included in case the trainer doubts the results of M8 or M9 detection.

In another example, a code T-800A simulates a false positive for a nerve agent, such as GB Sarin, and therefore, the simulant is window cleaner that causes M8 paper to turn yellow or gold. This simulates the possibility of GB Sarin, but is not conclusive. Therefore, a M256 TRAINS T-400 is used to simulate the absence of GB Sarin a blue color will be seen in detection window 106. Note that when the M8 color turns yellow or gold, the user selects detection window 106 for positioning the sample heater assembly 200 over by matching the yellow or gold to the M8 color comparator 114 (FIG. 1) and/or by matching the yellow or gold to the graphical symbol 442 on the backside 420 of a cover of a booklet containing the M8 paper (FIGS. 4A and 4B) and matching graphical symbol 442 to the shape of detection window 106.

For yet another example, a code T-800B simulates a false positive for a blister agent, and therefore, the simulant is xylene or benzene that causes M8 and M9 paper to turn red. This simulates the possibility of blister agent, but is not conclusive. Therefore, a M256 TRAINS T-400 is used to simulate the absence of blister agent, and a clear color will be generated in detection window 102. Note that when the color of the M8 paper turns red, the user selects detection window 102 for positioning the sample heater assembly 200 over by matching the red to the M8 color comparator 110 (FIGS. 1 and 3) and/or by matching the red to the M256 shape icon 440 on the backside 420 of the cover of the booklet containing the M8 paper (FIGS. 4A and 4B) and matching M256 shape icon (square) 440 to the shape of window 102.

In another example, a code T-800C simulates a false positive for a nerve agent, such as VX, and therefore, the simulant is DEET or brake fluid that causes M8 paper to turn green and M9 paper to turn red. This simulates the possibility of VX, but is not conclusive. Therefore, a M256 TRAINS T-400 is used to simulate the absence of VX. Note that when the color of the M8 paper turns green, the user selects detection window 106 for positioning the sample heater assembly 200 over by matching the green color to the M8 color comparator 112 (FIG. 1) and/or by matching the green to the M256 shape icon 444 (star) on the backside 420 of the cover of the booklet containing the M8 paper (FIGS. 4A and 4B) and matching M256 shape icon 444 to the shape of window 106.

In another example, a code T-801 simulates a POSITIVE for a nerve agent, such as GB Sarin, and therefore, the simulant is window cleaner that causes M8 paper to turn yellow or gold. This simulates the possibility of GB Sarin, but is not conclusive. Therefore, a M256 TRAINS T-401 is used to simulate the presence of GB Sarin. Note that when the M8 color turns yellow or gold, the user selects detection window 106 for positioning the sample heater assembly 200 over by matching the yellow or gold of the M8 to the M8 color comparator 114 (FIG. 1) and/or by matching the yellow or gold to the M256 shape icon (star) 442 on the backside 420 of a cover of a booklet containing the M8 paper (FIGS. 4A and 4B) and matching M256 shape icon 442 to the shape of window 106.

In another example, a code T-801A simulates a POSITIVE for a nerve agent, such as VX, and therefore, the simulant is DEET or brake fluid that causes M8 paper to turn green and M9 paper to turn red. This simulates the possibility of VX, but is not conclusive. Therefore, a M256 TRAINS T-401 is used to simulate the presence of VX. Note that when the color of the M8 paper turns green, the user selects detection window 106 for positioning the sample heater assembly 200 over by matching the green color of the M8 to the M8 color comparator 112 (FIG. 1) and/or by matching the green color to the M256 shape icon (star) 444 on the backside 420 of the cover of the booklet containing the M8 paper (FIGS. 4A and 4B) and matching M256 shape icon 444 to the shape of window 106.

For yet another example, a code T-802 simulates a POSITIVE for a blister agent, and therefore, the simulant is xylene or benzene that causes M8 and M9 paper to turn red. This simulates the possibility of blister agent, but is not conclusive. Therefore, a M256 TRAINS T-402 is used to simulate the presence of blister agent. Note that when the color of the M8 paper turns red, the user selects detection window 102 for positioning the sample heater assembly 200 over by matching the red color of the M8 to the M8 color comparator 110 (FIGS. 1 and 3) and/or by matching the red color of the M8 to the M256 shape icon (square) 440 on the backside 420 of the cover of the booklet containing the M8 paper (FIGS. 4A and 4B) and matching graphical symbol 440 to the shape of window 102.

CONCLUSION

Although specific embodiments have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A chemical detection training kit, comprising:
   one or more simulants selected from the group consisting of, benzene, xylene, glycol brake fluid, N—N diethyl m-toluamide, ammonia-containing glass cleaner, and fumed silica;
   chemical detection paper for receiving the one or more simulants, said detection paper selected from the group consisting of M8 and M9 chemical detection paper, and said paper producing a specific color change in response to said simulants;
   one or more detectors, each detector comprising an M256 TRAINS detector including a plurality of detection windows;
   a sample heating assembly for each of the one or more detectors, each sample heating assembly selectively positionable above different ones of the plurality of detection windows of said detector and having a reservoir for receiving said chemical detection paper having one of the one or more simulants absorbed thereon; and
   a heating element for each of the one or more detectors, each heating element positionable over the reservoir of said sample heating assembly to simulate heating said simulant received on said chemical detection paper.

2. The chemical detection training kit of claim 1, wherein said chemical detection paper is disposed in a booklet, wherein a cover of the booklet comprises a color key comprising a plurality of different colors, the different colors respectively corresponding to different graphical shapes formed on the cover, the different graphical shapes respectively corresponding to different shapes of the detection windows, wherein the different colors of the color key respectively correspond to different colors that the detection paper changes to in response to the detection paper receiving different simulants.

3. The chemical detection training kit of claim 1, wherein each detector includes a color code adjacent at least two of the detection windows, wherein each color code corresponds to a color that the detection paper changes to in response to the detection paper receiving different simulants.

4. The chemical detection training kit of claim 1, wherein the one or more detectors comprise an M256 TRAINS T-400, M256 TRAINS T-401 and M256 TRAINS T-402, which respectively simulate all clear, positive nerve, and positive blister.

5. The chemical detection training kit of claim 1, wherein each detector corresponds to a specific simulant.

6. The chemical detection training kit of claim 1, wherein each simulant simulates a low-volatility chemical warfare agent.

7. The chemical detection training kit of claim 1, wherein the chemical detection paper includes a sticky portion for adhering to solid simulants.

8. The chemical detection training kit of claim 1, wherein one or more of the detection windows of each detector contains an indicator, and wherein each detector further comprises one or more ampoules fluidly coupled to each of the detection windows, each ampoule containing a reagent that when caused to contact a corresponding indicator produces a color to simulate a presence or an absence of a hazard.

\* \* \* \* \*